United States Patent
Kweon et al.

(10) Patent No.: US 10,772,988 B2
(45) Date of Patent: *Sep. 15, 2020

(54) VASCULAR PATCH USING SILK MATRIX AND METHOD OF MANUFACTURING THE SAME

(71) Applicant: REPUBLIC OF KOREA(MANAGEMENT : RURAL DEVELOPMENT ADMINISTRATION), Jeonju-si, Jeollabuk-do (KR)

(72) Inventors: Hae-Yong Kweon, Suwon-si (KR); You-Young Jo, Jeollabuk-do (KR); Kwang-Gill Lee, Suwon-si (KR); Kee-Young Kim, Jeollabuk-do (KR)

(73) Assignee: Republic of Korea (Management: Rural Development Administration), Jeonju-si, Jeollabuk-do (KR)

( * ) Notice: Subject to any disclaimer, the term of this patent is extended or adjusted under 35 U.S.C. 154(b) by 21 days.

This patent is subject to a terminal disclaimer.

(21) Appl. No.: 15/762,308

(22) PCT Filed: Jun. 7, 2016

(86) PCT No.: PCT/KR2016/005965
§ 371 (c)(1),
(2) Date: Mar. 22, 2018

(87) PCT Pub. No.: WO2017/069367
PCT Pub. Date: Apr. 27, 2017

(65) Prior Publication Data
US 2018/0264170 A1 Sep. 20, 2018

(30) Foreign Application Priority Data

Oct. 21, 2015 (KR) .......... 10-2015-0146696

(51) Int. Cl.
*A61L 27/36* (2006.01)
*A61F 2/06* (2013.01)
(Continued)

(52) U.S. Cl.
CPC ........ *A61L 27/3604* (2013.01); *A61F 2/0063* (2013.01); *A61F 2/06* (2013.01);
(Continued)

(58) Field of Classification Search
CPC ........ A61F 2/06; A61F 2/0063; A61L 27/507; A61L 27/3604; B29C 43/003;
(Continued)

(56) References Cited

U.S. PATENT DOCUMENTS 9,539,154 B2 * 1/2017 Knight ............... A61L 27/3604
2009/0280161 A1 11/2009 Nakamura et al.
2012/0171256 A1 7/2012 Zhang et al.

FOREIGN PATENT DOCUMENTS

JP 63-036726 A 2/1988
JP 06-166850 A 6/1994
(Continued)

OTHER PUBLICATIONS

Ha, Y, et al "Comparison of the Physical Properties and In Vivo Bioactivities of Silkworm-Cocoon-Derived Silk Membrane, Collagen Membrane, and Polytetrafluoroethylene Membrane for Guided Bone Regeneration", Macromolecular Research, vol. 22, No. 9, pp. 1018-1023 (2014) (Year: 2014).*
(Continued)

*Primary Examiner* — Brian A Dukert
*Assistant Examiner* — Rebecca Lynee Zimmerman
(74) *Attorney, Agent, or Firm* — Rabin & Berdo, P.C.

(57) ABSTRACT

Disclosed are a vascular patch using a silk matrix and a method of manufacturing the same, wherein the vascular patch is configured such that a silk matrix having a cross-
(Continued)

section with a first thickness, produced from silkworms, is subjected to planar division into two or more silk matrix pieces having a predetermined shape with the first thickness. Furthermore, the manufacturing process is relatively simple, thus reducing the manufacturing cost compared to when manufacturing typical vascular patches, and also, the vascular patch can exhibit outstanding cell culture capacity and is biocompatible.

18 Claims, 8 Drawing Sheets

(51) Int. Cl.
  *A61F 2/00* (2006.01)
  *A61L 27/50* (2006.01)
(52) U.S. Cl.
  CPC ..... *A61L 27/507* (2013.01); *A61F 2230/0019* (2013.01); *A61F 2240/001* (2013.01)
(58) Field of Classification Search
  CPC .......... C07K 14/43586; C07K 2317/76; G01N 2333/43578
  See application file for complete search history.

(56) References Cited

FOREIGN PATENT DOCUMENTS

| | | | |
|---|---|---|---|
| JP | 2000-316422 A | 11/2000 | |
| JP | 2008-073408 A | 4/2008 | |
| JP | 2009-279214 A | 12/2009 | |
| JP | 2010-137041 A | 6/2010 | |
| KR | 10-2011-0023399 A | 3/2011 | |
| KR | 10-2013-0051602 A | 5/2013 | |
| KR | 10-1280722 B1 | 7/2013 | |
| KR | 10-2014-0130276 A | 11/2014 | |
| KR | 10-1602791 B1 | 3/2016 | |
| KR | 10-1602797 B1 | 3/2016 | |
| KR | 10-1651938 B1 | 8/2016 | |
| WO | WO-2011156586 A2 * | 12/2011 | .......... A61L 27/3604 |

OTHER PUBLICATIONS

Zhao, H. et al "Mechanical Properties of Silkworm Cocoons" Polymer, 46; 9192-9201 (2005) (Year: 2005).*
Garay, L.B., et al. (2014) "New Technique to Produce Large Amount of Flat Silk by Biospinning". Agricultural Sciences, 5, 1483-1490. (Year: 2014).*

* cited by examiner

VASCULAR PATCH USING SILK MATRIX AND METHOD OF MANUFACTURING THE SAME

TECHNICAL FIELD

The present invention relates to a vascular patch using a silk matrix and a method of manufacturing the same and, more particularly, to a vascular patch using a silk matrix and a method of manufacturing the same, wherein the vascular patch is biocompatible, is effective at maintaining the inner diameter of blood vessels, and promotes the growth of vascular endothelial cells in a vascular defect, unlike existing vascular patches.

BACKGROUND ART

During oral and maxillofacial surgery, vascular injuries may occur upon neck dissection, oral cancer removal or reconstruction, maxillofacial trauma, or surgical removal of lesions that are close to major blood vessels. Possible treatments for vascular injury may include the ligation of damaged blood vessels or the direct closure of vascular defects. However, when larger vessels such as the carotid artery, which are often encountered upon neck dissection, are subjected to ligation, various complications, such as cerebral infarction and the like, are reported to take place at high frequency. Furthermore, in the case where a vascular wall with a severe injury is forcibly treated by direct closure, the diameter of the blood vessel is narrowed, undesirably causing cerebral infarction due to vascular occlusion or neurological complications due to deterioration of the vascular function. Therefore, there is a critical need to develop simple methods and materials for treating damaged blood vessels to maintain the functions thereof and regenerate the vascular defects.

A vascular patch has been utilized upon cardiovascular damage in order to decrease complications such as vascular occlusion caused by a reduction in the diameter of the blood vessel due to direct closure. Numerous results comparing treatment of vascular damage via direct closure and treatment of vascular damage using a vascular patch have been reported, and reports in which better results are exhibited upon treatment using a vascular patch are dominant.

However, conventional vascular patches made of synthetic polymers (PET, ePTFE) or Gore-Tex cause vascular blockage due to thrombosis and also calcification due to bio-incompatibility, making it impossible to perform vascular functions for a long period of time. Furthermore, they are non-degradable materials and have low biocompatibility, undesirably incurring inflammation or tissue necrosis. Moreover, such vascular patches are expensive, and are difficult to apply to relatively thin blood vessels in oral and maxillofacial areas because they are custom made for cardiovascular applications.

Hence, there is ongoing research into vascular patches, which are made of natural materials, are biocompatible, and may retain the morphology of blood vessels without vaso-occlusive crisis.

Related techniques include one introduced at a Symposium in 2003 by Korea Society for Biotechnology and Bioengineering (Development of vascular patch using mesenchymal stem cells and biocompatible matrix) and Korean Patent Application Publication No. 10-2013-0051602 (3D Silk fibroin fiber characterized in dermal substitution and method of preparation for the same).

DISCLOSURE

Technical Problem

Accordingly, an object of the present invention is to provide a vascular patch using a silk matrix and a method of manufacturing the same, wherein the vascular patch is made of a biocompatible material, and thus has low foreign body reaction in tissue in vivo, and may grow endothelial cells without any inflammatory reaction to thus regenerate novel vascular walls, compared to existing vascular patches, and also, narrowing of the inner diameter of the blood vessel may be decreased, thereby maintaining the blood flow rate and the inner diameter of the blood vessel.

Another object of the present invention is to provide a vascular patch using a silk matrix and a method of manufacturing the same, wherein the manufacturing process is simple, and thus the manufacturing cost may be reduced compared to when manufacturing typical vascular patches.

The technical problem according to the present invention is not limited to the above objects, and other objects that are not described herein will be obviously understood by those having ordinary skill in the art from the following description.

Technical Solution

In order to accomplish the above objects, the present invention provides a vascular patch using a silk matrix, which is configured such that a silk matrix having a cross-section with a first thickness, produced from silkworms, is subjected to planar division into two or more silk matrix pieces having a predetermined shape with the first thickness.

In addition, the present invention provides a vascular patch using a silk matrix, which is configured such that a silk matrix having a cross-section with a first thickness, produced from silkworms, is subjected to thickness division into two or more silk matrix portions having a second thickness, which is less than the first thickness.

In addition, the present invention provides a vascular patch using a silk matrix, which is configured such that a silk matrix having a cross-section with a first thickness, produced from silkworms, is subjected to planar division into two or more silk matrix pieces having a predetermined shape with the first thickness, and each of the silk matrix pieces having the first thickness is subjected to thickness division into silk matrix pieces having a second thickness, which is less than the first thickness.

Advantageous Effects

According to the present invention, the vascular patch need not be removed in an additional process after having been used for a suture of a vascular defect, can exhibit outstanding cell culture capacity, and is effective at maintaining the blood flow rate and the inner diameter of the blood vessel, compared to existing vascular patches.

In addition, the method of manufacturing the vascular patch can reduce the manufacturing cost thanks to the simple manufacturing process, compared to when manufacturing typical vascular patches.

BEST MODE

Unless otherwise stated, the meanings of the terms, descriptions, etc., disclosed in the present specification may be those that are typically used in the art to which the present invention belongs. Hereinafter, a detailed description will be given of the present invention.

Conventional artificial vascular patches are mainly made of polyester and Gore-Tex (PTFE material). An artificial patch has to be applied taking into consideration the infection potential, vasodilation potential after anastomosis, vaso-occlusion due to thrombosis, bleeding via gaps between vascular suture materials, and the properties of the operational materials. Recently, a Gore-Tex patch has been developed by W. L. Gore (Flagstaff, Ariz., USA), but the results of long-term use thereof associated with expansion of blood vessels or neointimal hyperplasia have not yet been reported, and furthermore, it suffers from toxicity in vivo upon long-term use or remaining as a foreign material in vivo.

Therefore, in the present invention, the vascular patch using a silk matrix is manufactured, in which a biocompatible material is adopted, any inflammatory reaction does not readily occur upon in-vivo application, and outstanding cell adhesion and proliferation effects may be exhibited. Below is a description thereof, made with reference to various examples.

Figure 3:
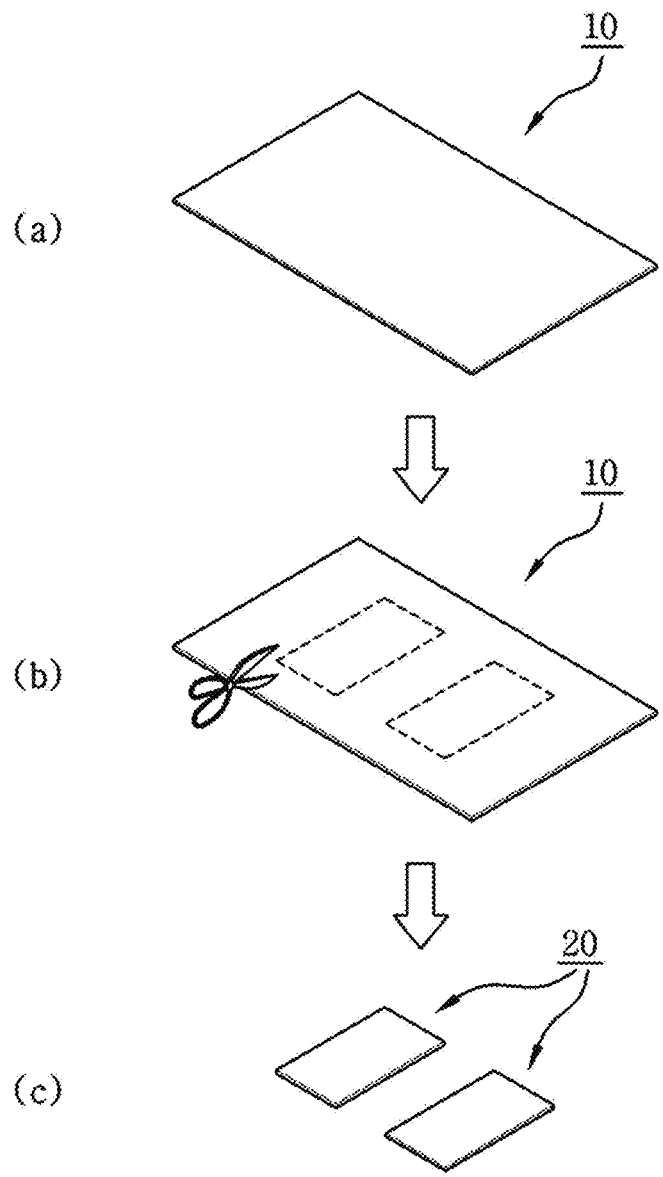
FIG. 3 illustrates the process of manufacturing the vascular patch of Example 1 according to the present invention.

The method of manufacturing a vascular patch using a silk matrix of Example 1 according to the present invention, as illustrated in FIG. 3, is specified below.

1. First Step: Preparation of Silk Matrix Pieces Having First Thickness

A silk matrix having a cross-section with a first thickness, produced from silkworms, is subjected to planar division into two or more pieces having an appropriate shape, thus obtaining silk matrix pieces having the first thickness.

When silkworms become mature silkworms to protect themselves, they begin to transform into pupae by spinning cocoons. When a silkworm transforms into a pupa, it spins a cocoon to make a pupal casing having a round and elongated shape. The casing is oval-shaped, and shows various colors depending on the kind of silkworm, and both ends thereof are slightly pointed and are thick. However, in the course of building cocoons by the silkworms, when a sheet on which the silkworms are placed is moved so as to disturb the formation of normal cocoons by the silkworms, silkworms do not make cocoons. The silkworms are artificially induced to spin cocoons on the sheet by moving the sheet on which the silkworms are placed, whereby the cocoons are spun in the form of a planar sheet, yielding a silk matrix.

Figure 1:
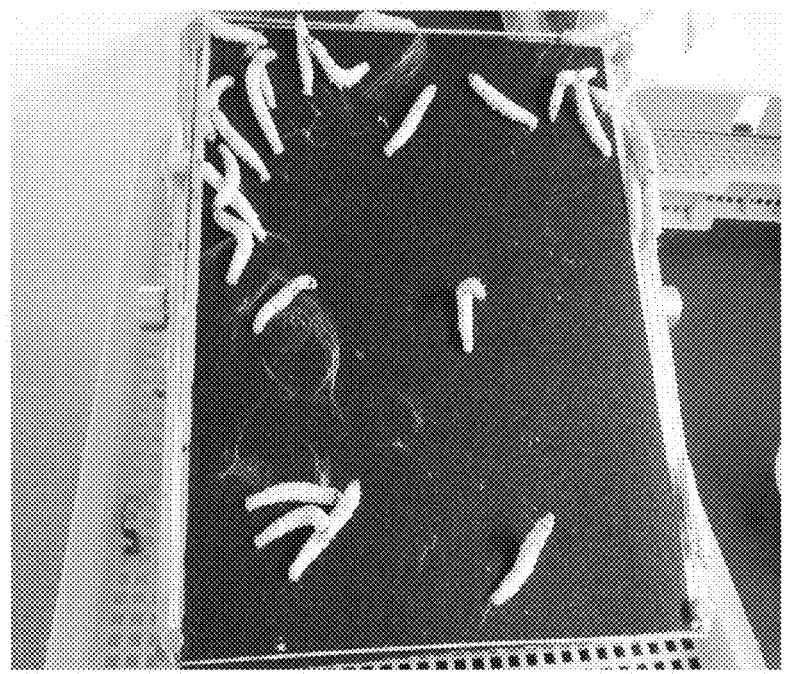
FIG. 1 illustrates the production of a silk matrix for use in a vascular patch according to the present invention, from silkworms.

Based on the above features, as illustrated in FIG. 1 according to an embodiment of the present invention, silkworms are placed on a sheet, and the sheet is tilted at a slope (15 to 30°) to an extent that the silkworms are prevented from falling off the sheet, so that the silkworms are forced to move on the sheet and induced to spin cocoons, thus preparing a silk matrix (FIGS. 2A and 2B), having a cross-section with a first thickness, of interest in the present invention, which is then subjected to planar division into two or more pieces having an appropriate shape so as to be suitable for desired applications, yielding silk matrix pieces 20 having the first thickness, as illustrated in FIG. 3. Briefly, the silk matrix having a cross-section with a first thickness is subjected to planar division using a cutter such as a blade or scissors, thus forming the silk matrix pieces 20 having the first thickness and an appropriate shape.

Figure 2:
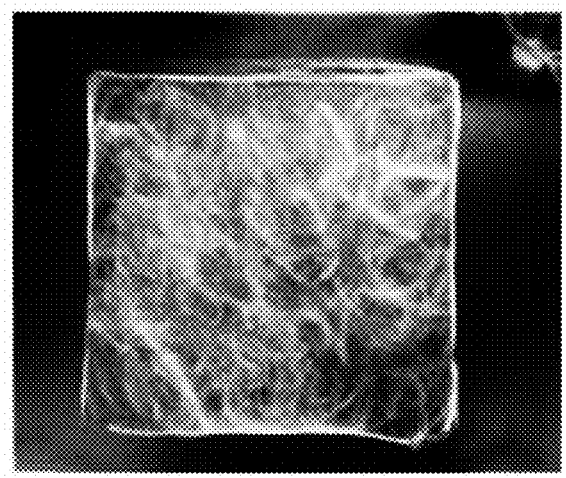
FIGS. 2A and 2B illustrate the results of visual observation of the morphology of the silk matrix at different thicknesses of 0.01 mm and 0.7 mm, respectively, used for a vascular patch according to the present invention.
Figure 2:

As illustrated in FIG. 2A, the silk matrix pieces 20 having the first thickness and the appropriate shape, obtained by subjecting the silk matrix 10 having the first thickness to planar division, may be used unchanged because the silk matrix 10 having the first thickness is produced to a thickness suitable for use as a vascular patch. Further, packing or sterile treatment and chemical treatment may be additionally performed, as necessary. For example, thrombosis may be inhibited by the use of 4-hexylresorcinol, which is an antithrombotic component.

In the case where the sheet on which silkworms are placed is moved to form a silk matrix, the movement thereof may be carried out variously. The sheet may be moved in a manner of being rotated, repeatedly tilted upward and downward and/or leftward and rightward, or vibrated. Alternatively, the sheet may be moved through a combination of rotation and repeated tilting upward and downward and/or leftward and rightward. The number or rate of movement or tilting processes may be appropriately set in order to ensure that the silk matrix has the desired shape.

The shape of the sheet on which silkworms are placed is not limited. A circular shape or a rectangular shape may be applied. Alternatively, any shape may be applied so long as silkworms do not spin cocoons normally in response to the movement of the sheet.

Figure 4:
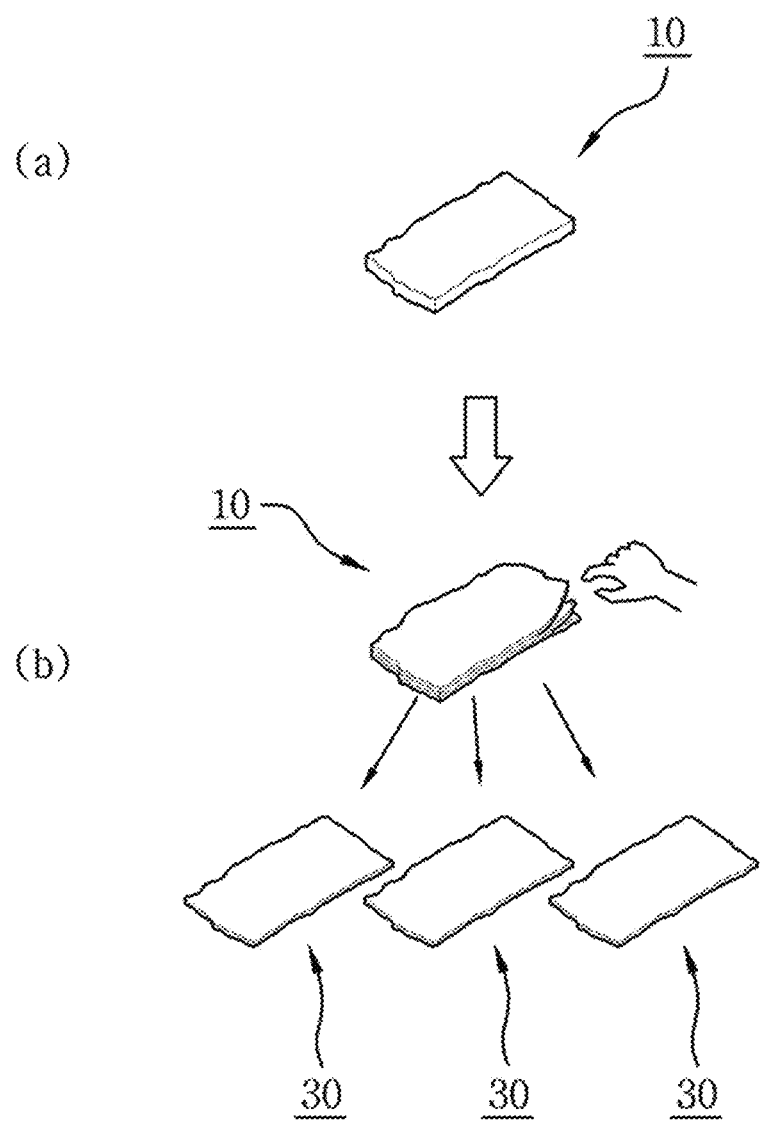
FIG. 4 illustrates the process of manufacturing the vascular patch of Example 2 according to the present invention.

In another modification, the method of manufacturing a vascular patch using a silk matrix of Example 2 according to the present invention, as illustrated in FIG. 4, is specified below.

1. First Step: Preparation of Silk Matrix Portions Having Second Thickness

A silk matrix having a cross-section with a first thickness, produced from silkworms, is subjected to thickness division into two or more portions having a second thickness, which is less than the first thickness.

The silk matrix 10 having the first thickness is produced from silkworms in such a manner that silkworms spin cocoons while being forced to move on the sheet, as in the description of FIG. 3. The silk matrix 10 having the first thickness may be configured as illustrated in FIG. 2B such that yarns resulting from spinning cocoons from the silkworms are stacked in a height direction to thus form various thicknesses (multiple layers).

The first thickness of the silk matrix 10 may vary depending on the number of silkworms used to prepare the silk matrix and the period of time that the silkworms require to spin cocoons.

As shown in FIG. 4, when the silk matrix 10 having the first thickness is thick, it may be subjected to thickness division into two or more portions having a thickness suitable for use in a vascular patch, thus forming silk matrix portions 30 having a second thickness. The second thickness is less than the first thickness owing to such thickness division.

The silk matrix portions 30 having the second thickness may be used unchanged as the vascular patch. Alternatively, portions of the silk matrix portions 30 having the second thickness may be utilized by adjusting the size thereof so as to be suitable for some end use. Further, packing or sterile treatment and chemical treatment may be additionally performed, as necessary. For example, thrombosis may be inhibited by the use of 4-hexylresorcinol, which is an antithrombotic component.

Figure 5:
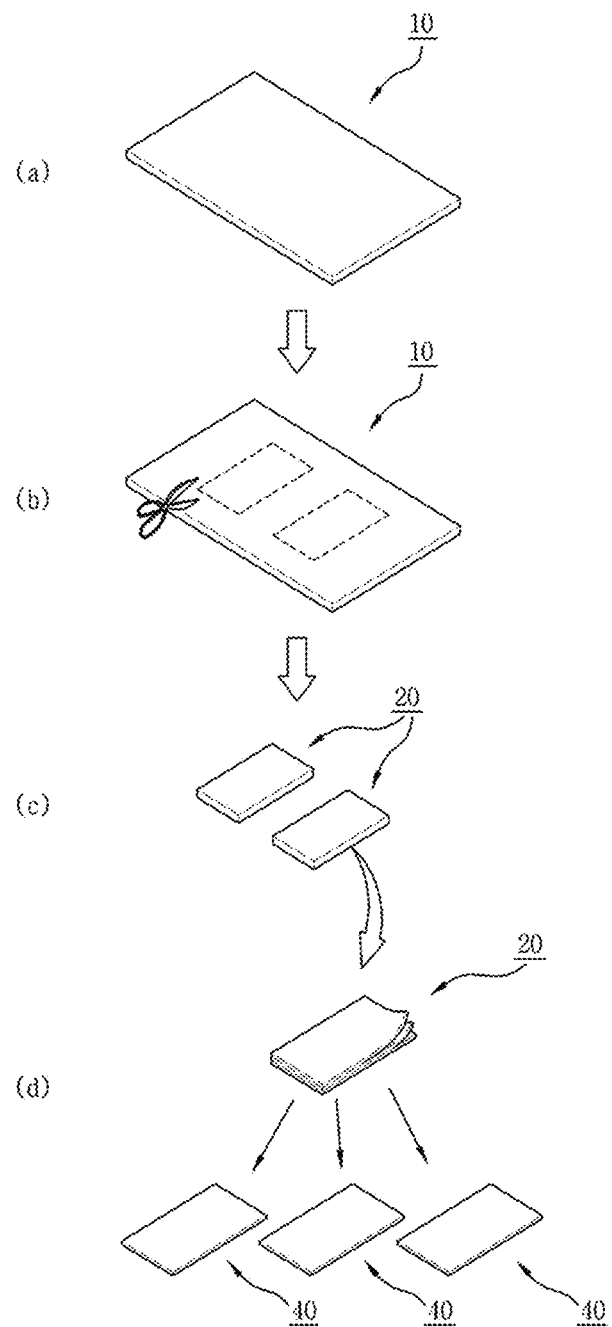
FIG. 5 illustrates the process of manufacturing the vascular patch of Example 3 according to the present invention.

In a further modification, the method of manufacturing a vascular patch using a silk matrix of Example 3 according to the present invention, as illustrated in FIG. 5, is specified below.

1. First Step: Preparation of Silk Matrix Pieces Having First Thickness

A silk matrix having a cross-section with a first thickness, produced from silkworms, is subjected to planar division into two or more pieces having an appropriate shape, thus forming silk matrix pieces 20 having the first thickness.

In this case, the silk matrix pieces 20 having the first thickness are formed in the same manner as in the first step of the description of FIG. 3.

When the first thickness of the silk matrix pieces 20 thus formed is suitable for use in a vascular patch, such silk matrix pieces may be used without change. In the case where the silk matrix pieces are thick and difficult to use, they should be additionally subjected to the following second step so as to have a thickness suitable for vascular patches. The second step is described below.

2. Second Step: Preparation of Silk Matrix Pieces (Vascular Patch) Having Second Thickness Silk matrix pieces 40 having a second thickness, suitable for use as a vascular patch, are prepared.

The silk matrix pieces 20 having the first thickness, obtained in the first step, are configured as illustrated in FIG. 2B such that yarns resulting from spinning cocoons from the silkworms are stacked in a height direction to thus form various thicknesses (multiple layers).

The first thickness of the silk matrix pieces 20 may vary depending on the number of silkworms used to prepare the silk matrix and the period of time that the silkworms require to spin cocoons.

When the silk matrix pieces 20 having the first thickness are suitable for use in a vascular patch, they may be used without change. As illustrated in FIG. 5, in the case where the silk matrix pieces are thick, each of the silk matrix pieces having the first thickness, obtained in the first step, is subjected to thickness division into two or more pieces having an appropriate thickness so as to serve as a vascular patch, yielding silk matrix pieces 40 having a second thickness. As such, the second thickness is less than the first thickness owing to the thickness division.

The silk matrix pieces 40 having a second thickness may be used unchanged as a vascular patch for any purpose. Further, packing or sterile treatment and chemical treatment may be additionally performed, as necessary. For example, thrombosis may be inhibited by the use of 4-hexylresorcinol, which is an antithrombotic component.

A better understanding of the present invention may be obtained through the following examples and test examples, which are set forth to illustrate, but are not to be construed to limit the scope of the present invention.

<Example 1> Manufacture of Vascular Patch 1 of the Invention

As illustrated in FIG. 1, 15 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2A.

The above tilting process was performed for one day, equilibrium was maintained for two days, and the above tilting process was performed again, whereby a silk matrix was produced from the silkworms in about three days. The silk matrix had a thickness of about 0.01 mm.

As shown in FIG. 3, the silk matrix 10 was cut using scissors so as to undergo planar division in a rectangular shape, thus forming silk matrix pieces 20, which were then sterilized, thereby manufacturing a vascular patch 1 according to the present invention.

<Example 2> Manufacture of Vascular Patch 2 of the Invention

As illustrated in FIG. 1, 30 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2B.

The above tilting process was performed for one day, equilibrium was maintained for two days, and the above tilting process was performed again, whereby a silk matrix was produced from the silkworms in about three days. The silk matrix had a thickness of about 0.7 mm.

As shown in FIG. 4, the silk matrix 10 having a thickness of 0.7 mm was peeled so as to undergo thickness division, thus forming silk matrix portions 30 having a thickness of 0.2 mm, which were then sterilized, thereby manufacturing a vascular patch 2 according to the present invention.

<Example 3> Manufacture of Vascular Patch 3 of the Invention

As illustrated in FIG. 1, 30 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2B.

The above tilting process was performed for one day, equilibrium was maintained for two days, and the above tilting process was performed again, whereby a silk matrix was produced from the silkworms in about three days. The silk matrix had a thickness of about 0.7 mm.

The silk matrix was then cut to undergo planar division in a rectangular shape, thus forming silk matrix pieces 20.

As illustrated in FIG. 5, the silk matrix pieces 20 having a thickness of 0.7 mm were peeled so as to undergo thickness division, thus obtaining silk matrix pieces 40 having a thickness of 0.2 mm, after which 10 g of the silk matrix pieces 40 was immersed for 24 hr in a 3% solution of 4-hexylresorcinol as an antithrombotic agent. The silk matrix pieces 40 impregnated with 4-hexylresorcinol were placed in a dry oven at 45° C. so as to volatilize alcohol. After evaporation of the alcohol, the resulting silk matrix had a weight of 10.3 g, followed by a sterilization process (ethylene oxide (EO) gas), yielding a vascular patch 3 according to the present invention.

<Example 4> Manufacture of Vascular Patch 4 of the Invention

A vascular patch 4 according to the present invention was manufactured in the same manner as in Example 3, with the exception that silk matrix pieces 40 having a thickness of 0.3 mm were formed.

<Example 5> Manufacture of Vascular Patch 5 of the Invention

A vascular patch 5 according to the present invention was manufactured in the same manner as in Example 3, with the exception that silk matrix pieces 40 having a thickness of 0.5 mm were formed.

<Test Example 1> Evaluation of Morphology of Silk Matrix Used for Vascular Patch of the Invention 1. Test Method In order to evaluate the morphology of the silk matrix of FIGS. 2A and 2B, it was observed at a predetermined magnification using SEM, and the surface of a commercially available Gore-Tex vascular patch was observed as a control.

2. Test Results

Figure 6:
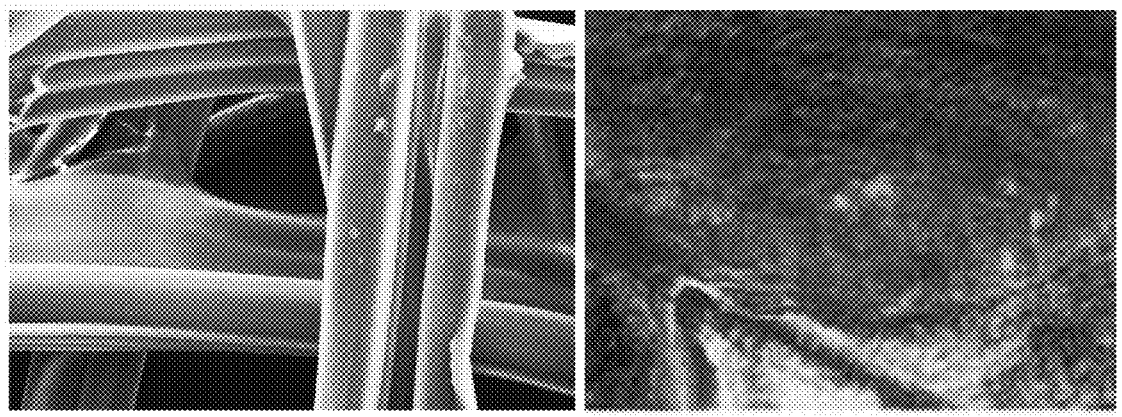
FIG. 6 illustrates the scanning electron microscopy (SEM) images of the surface morphologies of the vascular patch using the silk matrix according to the present invention and the Gore-Tex vascular patch used as a control.

As illustrated in FIG. 6, when the morphologies of the vascular patches of the present invention and the control were observed using SEM, there was a morphological difference in terms of the pore shape or the membrane surface. As for the vascular patch made of Gore-Tex, pores having a predetermined interval and size were observed on the surface of the planar membrane.

However, the surface of the vascular patch of the present invention was configured such that fiber strands having various thicknesses were repeatedly irregularly stacked, and many pores could be observed between the stacked fiber strands. Thus, the vascular patch of the present invention has a porous structure and is thus deemed to be effective at maintaining the blood flow rate and the inner diameter of blood vessels.

<Test Example 2> Measurement of Mechanical Properties of Vascular Patch of the Invention In order to measure the mechanical properties of the vascular patch using the silk matrix according to the present invention, tensile testing was performed using a universal testing machine (DAEYEONG, Korea).

Analytical samples were manufactured to a size of 2.5× 0.07 (width×length) mm, and the manufactured membrane was stretched at a gauge length of 10 mm and a rate of 10 mm/min.

The results are shown in Table 1 below.

TABLE 1

| Kind | Tensile strength (MPa) | Elongation (%) |
|---|---|---|
| Vascular patch of Example 3 | 21.51 ± 1.7 | 12.04 ± 1.2 |
| Vascular patch of Example 4 | 24.18 ± 1.9 | 15.35 ± 1.4 |
| Vascular patch of Example 5 | 32.23 ± 2.6 | 17.52 ± 1.7 |

As is apparent from Table 1, the vascular patches of the present invention were different in tensile strength and elongation depending on the thickness, and the tensile strength and elongation of the vascular patch were increased with an increase in the thickness thereof.

<Test Example 3> Ultrasonic Analysis

1. Test Method
(1) Suture of Vascular Defect

The vascular defect was sutured using the vascular patch of Example 3. This test was performed using seven white rats. Specifically, the right carotid artery portion of each white rat was shaved and the skin thereof was disinfected. At the exposed right carotid artery portion, a vascular defect having a size of 0.5×1 mm was formed using microscissors. The formed defect was reconstructed using the above vascular patch, and the vascular patch was fixed using 10-0 monofilament nylon (Ailee, Korea).

As a control 1, a commercially available Gore-Tex vascular patch was used, and a vascular defect was sutured in the same manner as above.

As a control 2, a vascular defect was sutured through direct closure using 10-0 monofilament nylon (Ailee, Korea).

Figure 7:
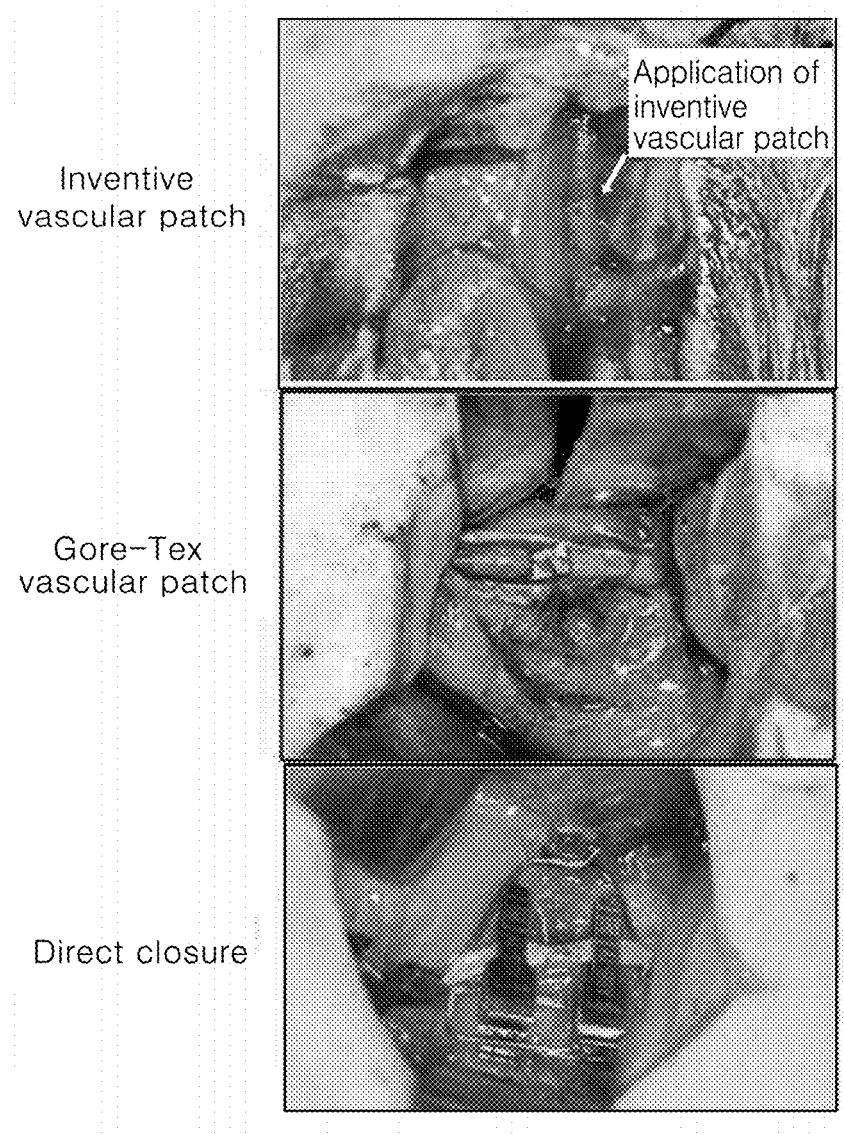
FIG. 7 illustrates the suture images of vascular defects using the vascular patch of the invention, the Gore-Tex vascular patch as a control, and the direct closure as another control.

The suture images of the vascular defects through individual processes are illustrated in FIG. 7.

(2) Ultrasonic Analysis

In order to evaluate the circulation and stenosis of the sutured vascular defect, ultrasonic analysis was performed. As an ultrasonic factor, peak systolic velocity (PSV) was measured, and thus whether the vascular functional regeneration was achieved was evaluated.

2. Test Results

Figure 8:
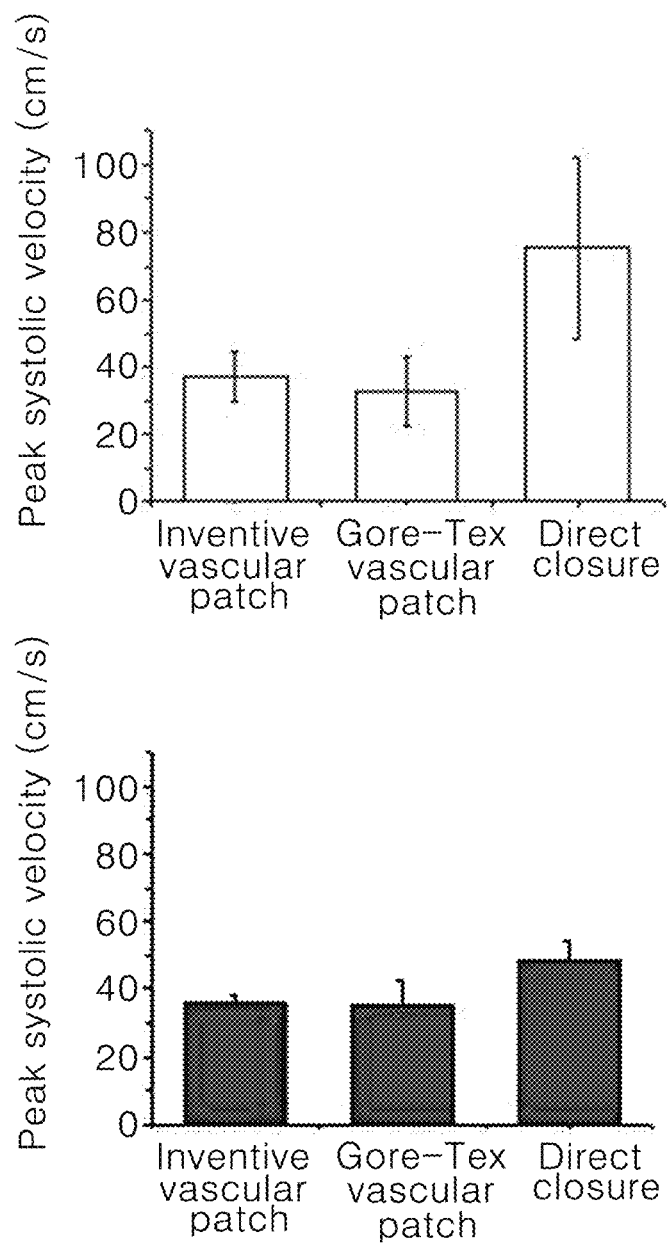
FIG. 8 is a graph illustrating the peak systolic velocity, one week and three weeks after the vascular defects were sutured.

FIG. 8 is a graph illustrating the PSV values, one week and three weeks after the vascular defects were sutured. In the graph of FIG. 8, one week after the vascular defects were sutured, the PSV was measured to be 37.26±7.26 cm/s when using the vascular patch of the invention, 32.74±10.50 cm/s when using the Gore-Tex vascular patch as the control 1, and 75.23±27.05 cm/s upon direct closure. Based on the results of analysis of variance (ANOVA), the differences between the three groups were found to be statistically significant ($p=0.007$).

In the graph of FIG. 8, three weeks after the vascular defects were sutured, the PSV was measured to be 35.67±2.62 cm/s for the vascular patch of the invention, 35.36±7.27 cm/s for the Gore-Tex vascular patch as the control 1, and 48.36±6.15 cm/s upon direct closure as the control 2. Based on the results of analysis of variance (ANOVA), the differences between the three groups were found to be statistically significant ($p=0.007$).

After the vascular patch was transplanted into the external carotid of the white rat, changes in the PSV of the blood vessel were measured. In conclusion, the vascular patch of the present invention had a PSV (cm/s) change of 20% or less, particularly ranging from 1% to 20%. Therefore, the vascular patch using the silk matrix according to the present invention showed that the PSV change was stably maintained.

<Test Example 4> Histological Analysis

1. Test Method

Figure 9:
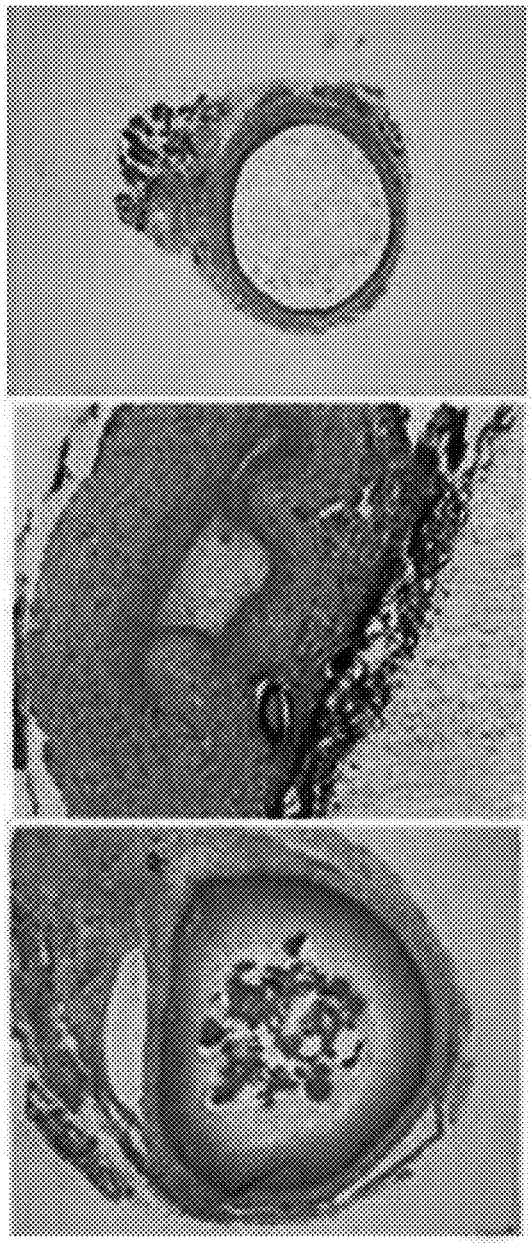
FIG. 9 illustrates the cross-sectional images of tissues, two weeks after the vascular defects were repaired using the vascular patch of the invention, the Gore-Tex vascular patch as a control, and the direct closure as another control.

In order to measure the thickness of the vascular wall of the sutured vascular defect and the diameter of the blood vessel and to evaluate whether a foreign body reaction was caused by the vascular patch, histological analysis was performed. Specifically, both sides of the blood vessel were ligated to maintain the diameter of the blood vessel, and both vessels were sampled under the condition that blood was retained in the vessel. The vascular samples thus obtained were immobilized with alcohol. The vascular samples were stained with hematoxylin and eosin. The cross-sections of the immobilized and stained vascular samples were observed. FIG. 9 illustrates the cross-sections of the tissues two weeks after the vascular suture using the vascular patch of the invention (Example 3), the Gore-Tex patch as the control 1 and the direct closure as the control 2.

2. Test Results

As illustrated in FIG. 9, based on histological results, no foreign body reaction was observed around the vascular patch using the silk matrix according to the present invention. The reconstructed vascular wall was not specifically distinguished from the peripheral tissue, and the inner diameter of the blood vessel was maintained. As for the control using the Gore-Tex vascular patch, the inner diameter of the blood vessel was not changed much, but overgrowth of the internal wall of the blood vessel was caused in some samples. As for the control through direct closure, the inner diameter of the blood vessel was considerably narrowed.

Therefore, the vascular patch according to the present invention remarkably reduced overgrowth of the vascular wall and narrowing of the inner diameter of the blood vessel, and was thus effective at maintaining the blood flow rate and the inner diameter of the blood vessel, compared to when using a conventional Gore-Tex vascular patch or direct closure.

Although the preferred examples and test examples of the present invention have been disclosed for illustrative purposes, those skilled in the art will appreciate that various modifications, additions and substitutions are possible, without departing from the scope and spirit of the invention as disclosed in the accompanying claims. The scope of the present invention is shown not in the above description but in the claims, and all differences within the range equivalent thereto will be understood to be incorporated in the present invention.

The invention claimed is:

1. A method of manufacturing a vascular patch using a silk matrix, comprising:
    placing silkworms on a sheet;
    inducing the silkworms to spin the silk matrix on the sheet by moving the sheet and forming the silk matrix by preventing the silkworms from falling off the sheet and forming a pupal casing with the cocoons, the silk matrix having a cross-section with a first thickness,
    wherein the sheet is moved in a manner of being rotated, repeatedly tilted upward and downward, or vibrated; and
    subjecting the silk matrix to planar division into two or more silk matrix pieces having a predetermined shape with the first thickness.

2. A method of manufacturing a vascular patch using a silk matrix, comprising:
    placing silkworms on a sheet;
    inducing the silkworms to spin the silk matrix on the sheet by moving the sheet and forming the silk matrix by preventing the silkworms from falling off the sheet and forming a pupal casing with the cocoons, the silk matrix having a cross-section with a first thickness,
    wherein the sheet is moved in a manner of being rotated, repeatedly tilted upward and downward, or vibrated; and
    subjecting the silk matrix to thickness division into two or more silk matrix portions having a second thickness, which is less than the first thickness.

3. A method of manufacturing a vascular patch using a silk matrix, comprising:
    placing silkworms on a sheet;
    inducing the silkworms to spin the silk matrix on the sheet by moving the sheet and forming the silk matrix by preventing the silkworms from falling off the sheet and forming a pupal casing with the cocoons, the silk matrix having a cross-section with a first thickness,
    wherein the sheet is moved in a manner of being rotated, repeatedly tilted upward and downward, or vibrated;
    subjecting the silk matrix to planar division into two or more silk matrix pieces having a predetermined shape with the first thickness; and
    subjecting each of the silk matrix pieces having the first thickness to thickness division into two or more silk matrix pieces having a second thickness, which is less than the first thickness.

4. The method of claim 1, further comprising stacking the silk matrix pieces having the first thickness obtained in the first step.

5. The method of claim 2, further comprising stacking the silk matrix portions having the second thickness obtained in the first step.

6. The method of claim 3, further comprising stacking the silk matrix pieces having the second thickness obtained in the second step.

7. The method of any one of claim 1, further comprising performing at least one sterilization process, before or after each step.

8. The method of any one of claim 2, further comprising performing at least one sterilization process, before or after each step.

9. The method of any one of claim 3, further comprising performing at least one sterilization process, before or after each step.

10. The method of any one of claim 4, further comprising performing at least one sterilization process, before or after each step.

11. The method of any one of claim 5, further comprising performing at least one sterilization process, before or after each step.

12. The method of any one of claim 6, further comprising performing at least one sterilization process, before or after each step.

13. A method of manufacturing a vascular patch for a vascular defect using a silk matrix, comprising: providing silkworms for making the silk matrix; forming the silk matrix by preventing the silkworms from forming a pupal casing with the cocoons, the silk matrix having a cross-section with a first thickness; subjecting the silk matrix to planar division into two or more silk matrix pieces having a predetermined shape with the first thickness; wherein one of the two or more silk matrix pieces is constructed to apply to the vascular defect of a subject.

14. A method of manufacturing a vascular patch for a vascular defect using a silk matrix, comprising: providing silkworms for making the silk matrix; forming the silk matrix by preventing the silkworms from forming a pupal casing with the cocoons, the silk matrix having a cross-section with a first thickness; subjecting the silk matrix to thickness division into two or more silk matrix portions having a second thickness, which is less than the first thickness; wherein one of the two or more silk matrix pieces is constructed to apply to the vascular defect of a subject.

15. A method of manufacturing a vascular patch for a vascular defect using a silk matrix, comprising: providing silkworms for making the silk matrix: forming the silk matrix by preventing the silkworms from forming a pupal casing with the cocoons, the silk matrix having a cross-section with a first thickness; subjecting the silk matrix to planar division into two or more silk matrix pieces having a predetermined shape with the first thickness; subjecting each of the silk matrix pieces having the first thickness to thickness division into two or more silk matrix pieces having a second thickness, which is less than the first thickness; wherein one of the two or more silk matrix pieces is constructed to apply to the vascular defect of a subject.

16. The method claim 13, further comprising performing at least one sterilization process, before or after each step.

17. The method claim 14, further comprising performing at least one sterilization process, before or after each step.

18. The method claim 15, further comprising performing at least one sterilization process, before or after each step.

* * * * *